United States Patent
Harvey et al.

(10) Patent No.: US 11,269,029 B2
(45) Date of Patent: Mar. 8, 2022

(54) MAGNETIC RESONANCE EXAMINATION SYSTEM WITH A MOVEABLE PATIENT CARRIER

(71) Applicant: KONINKLIJKE PHILIPS N.V., Eindhoven (NL)

(72) Inventors: Paul Royston Harvey, Eindhoven (NL); Cornelis Leonardus Gerardus Ham, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 201 days.

(21) Appl. No.: 15/550,810

(22) PCT Filed: Feb. 18, 2016

(86) PCT No.: PCT/EP2016/053486
§ 371 (c)(1),
(2) Date: Aug. 14, 2017

(87) PCT Pub. No.: WO2016/135045
PCT Pub. Date: Sep. 1, 2016

(65) Prior Publication Data
US 2018/0031649 A1 Feb. 1, 2018

(30) Foreign Application Priority Data
Feb. 27, 2015 (EP) .................................... 15156948

(51) Int. Cl.
*G01R 33/30* (2006.01)
*G01R 33/563* (2006.01)
(Continued)

(52) U.S. Cl.
CPC ............ *G01R 33/307* (2013.01); *A61B 5/055* (2013.01); *A61B 5/704* (2013.01); *G01R 33/28* (2013.01);
(Continued)

(58) Field of Classification Search
CPC ....... A61B 5/055; A61B 5/0555; A61B 5/704; A61B 5/7203; G01R 33/28; G01R 33/307;
(Continued)

(56) References Cited

U.S. PATENT DOCUMENTS 4,629,989 A * 12/1986 Riehl ................... A61B 5/0555
324/300
6,211,677 B1 * 4/2001 Burl ....................... G01R 33/36
324/322
(Continued)

FOREIGN PATENT DOCUMENTS

| CN | 101292872 A | 10/2008 |
| JP | 04105643 A | 4/1992 |

(Continued)

OTHER PUBLICATIONS

Muthupillai et al. (Sep. 29, 1995). "Magnetic resonance elastography by direct visualization of propagating acoustic strain waves" Science. 269 (5232): 1854-7. (Year: 1995).*

*Primary Examiner* — Pascal M Bui Pho
*Assistant Examiner* — Alexei Bykhovski

(57) ABSTRACT

In a magnetic resonance examination system, the patient carrier is mounted moveably in a direction transverse to the support surface and an RF antenna has a fixed geometrical relation to the support surface.

14 Claims, 2 Drawing Sheets

(51) Int. Cl.
  *G01R 33/567* (2006.01)
  *A61B 5/00* (2006.01)
  *A61B 5/055* (2006.01)
  *G01R 33/28* (2006.01)
  *G01R 33/3415* (2006.01)

(52) U.S. Cl.
  CPC ... *G01R 33/5673* (2013.01); *G01R 33/56358* (2013.01); *A61B 5/7203* (2013.01); *G01R 33/3415* (2013.01)

(58) Field of Classification Search
  CPC .......... G01R 33/3415; G01R 33/56358; G01R 33/5673
  See application file for complete search history.

(56) References Cited

U.S. PATENT DOCUMENTS

| | | | |
|---|---|---|---|
| 6,529,004 B1 | 3/2003 | Young | |
| 2003/0078489 A1* | 4/2003 | DeSilets | A61B 6/0457 600/407 |
| 2004/0263171 A1 | 12/2004 | Yamagata | |
| 2005/0122108 A1 | 6/2005 | Yasuhara et al. | |
| 2008/0216844 A1* | 9/2008 | Olfert | A61B 6/4423 128/856 |
| 2008/0267358 A1 | 10/2008 | Hiyama | |
| 2009/0189608 A1* | 7/2009 | Liu | A61B 5/055 324/321 |
| 2009/0306494 A1 | 12/2009 | Scarth et al. | |
| 2013/0303882 A1* | 11/2013 | Kolipaka | A61B 5/0555 600/415 |
| 2014/0232395 A1 | 8/2014 | Sutton et al. | |
| 2015/0011869 A1* | 1/2015 | Piferi | A61B 5/0555 600/415 |
| 2015/0201891 A1* | 7/2015 | Padwa | A61B 6/467 600/425 |
| 2015/0369888 A1* | 12/2015 | Calvert | G01R 33/3854 324/307 |

FOREIGN PATENT DOCUMENTS

| | | |
|---|---|---|
| JP | 2005131103 A | 5/2005 |
| JP | 2008220647 A | 9/2008 |
| WO | 2013153493 A1 | 4/2013 |

* cited by examiner

MAGNETIC RESONANCE EXAMINATION SYSTEM WITH A MOVEABLE PATIENT CARRIER

CROSS REFERENCE TO RELATED APPLICATIONS

This application is a U.S. national phase application of International Application No. PCT/EP2016/053486, filed on Feb. 18, 2016, which claims the benefit of EP Application Serial No. 15156948.0 filed on Feb. 27, 2015 and is incorporated herein by reference.

FIELD OF THE INVENTION

The invention pertains to a magnetic resonance examination system with a moveable patient carrier.

BACKGROUND OF THE INVENTION

A magnetic resonance examination system with a moveable patient carrier is known from the international application WO2013/153493.

Magnetic resonance imaging (MRI) methods utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MRI method in general, the body of the patient to be examined is arranged in a strong, uniform magnetic field $B_0$ whose direction at the same time defines an axis (normally the z-axis) of the co-ordinate system to which the measurement is related. The magnetic field $B_0$ causes different energy levels for the individual nuclear spins in dependence on the magnetic field strength which can be excited (spin resonance) by application of an electromagnetic alternating field (RF field) of defined frequency (so-called Larmor frequency, or MR frequency). From a macroscopic point of view the distribution of the individual nuclear spins produces an overall magnetisation which can be deflected out of the state of equilibrium by application of an electromagnetic pulse of appropriate frequency (RF pulse) while the corresponding magnetic field $B_1$ of this RF pulse extends perpendicular to the z-axis, so that the magnetization performs a precession motion about the z-axis. The precession motion describes a surface of a cone whose angle of aperture is referred to as flip angle. The magnitude of the flip angle is dependent on the strength and the duration of the applied electromagnetic pulse. In the example of a so-called 90° pulse, the magnetization is deflected from the z axis to the transverse plane (flip angle 90°).

After termination of the RF pulse, the magnetization relaxes back to the original state of equilibrium, in which the magnetization in the z direction is built up again with a first time constant T1 (spin lattice or longitudinal relaxation time), and the magnetization in the direction perpendicular to the z-direction relaxes with a second and shorter time constant T2 (spin-spin or transverse relaxation time). The transverse magnetization and its variation can be detected by means of receiving RF antennae (coil arrays) which are arranged and oriented within an examination volume of the magnetic resonance examination system in such a manner that the variation of the magnetization is measured in the direction perpendicular to the z-axis. The decay of the transverse magnetization is accompanied by dephasing taking place after RF excitation caused by local magnetic field inhomogeneities facilitating a transition from an ordered state with the same signal phase to a state in which all phase angles are uniformly distributed. The dephasing can be compensated by means of a refocusing RF pulse (for example a 180° pulse). This produces an echo signal (spin echo) in the receiving coils.

In order to realize spatial resolution in the subject being imaged, such as a patient to be examined, magnetic field gradients extending along the three main axes are superposed on the uniform magnetic field $B_0$, leading to a linear spatial dependency of the spin resonance frequency. The signal picked up in the receiving antennae (coil arrays) then contains components of different frequencies which can be associated with different locations in the body. The signal data obtained via the receiving coils correspond to the spatial frequency domain of the wave-vectors of the magnetic resonance signal and are called k-space data. The k-space data usually include multiple lines acquired of different phase encoding. Each line is digitised by collecting a number of samples from k-space. A set of k-space data is converted to an MR image by means of Fourier transformation.

The transverse magnetization dephases also in presence of constant magnetic field gradients. This process can be reversed, similar to the formation of RF induced (spin) echoes, by appropriate gradient reversal forming a so-called gradient echo. However, in case of a gradient echo, effects of main field inhomogeneities, chemical shift and other off-resonances effects are not refocused, in contrast to the RF refocused (spin) echo.

The known magnetic resonance examination system has a main magnet with a bore that provides a region of examination. An RF antenna is mounted fixedly in the bore. A patient table top is provided for a patient to lie in the bore during an MR examination. The position of the patient table top relative to the RF antenna is adjustable to bring the patient closer to the RF antenna.

The U.S. Pat. No. 4,629,989 concerns the problem to position the patient to be examined in the optimum homogeneous region of the polarising magnetic field. To that end the known patient alignment system utilises laser light sources to create a visible reference point. A longitudinal drives system can move the patient cradle head-first or feet first.

SUMMARY OF THE INVENTION

An object of the invention is to provide a magnetic resonance examination system in which the position of patient to be examined can be better adjusted in the static magnetic field of the magnetic resonance examination system.

This object is achieved in a magnetic resonance examination system of the invention comprising
  an examination zone
  a magnet to apply a static magnetic field in the examination zone
  a patient carrier with a support surface
    an RF antenna having a fixed geometrical relation to the support surface, wherein
    the patient carrier is mounted moveably in a direction transverse to the support surface.

In the magnetic resonance examination system the RF antenna to pick-up magnetic resonance signal from the patient to be examined is located at a fixed geometrical relationship to the patient to be examined. In the examination zone the static magnetic field is applied and an RF excitation field can be generated, e.g. by the RF antenna operated in transmit mode or by way of a separate transmit antenna. The part of the body of the patient to be examined is placed in the examination zone where RF excitations can be applied to the spins in the patient's body and magnetic resonance signal from the patient's body can be acquired. By mounting the RF antenna to the patient carrier or by placing the RF antenna on the body of the patient to be examined, the RF antenna to receive the magnetic resonance signal is located at a fixed geometrical relationship to the patient to be examined. This achieves an optimum distance between the RF antenna and the body of the patient to be examined for acquisition of the magnetic resonance signals. Because the patient carrier is moveable transverse to the support surface of the patient carrier, the position of region-of-interest of the body of the patient to be examined can be better adjusted in a region of very good spatial homogeneity of the static magnetic field. In this region of good spatial homogeneity, the main magnetic field has a high degree of spatial uniformity and preferably also gradient magnetic fields have at most a very small deviation form linearity. The support surface is the surface on which the patient's body is placed on the patient carrier. For example, the patient may be placed directly on the table top or the patient may be placed on a thin mattress that is placed on the table top. In these examples the support surface is formed by the surface of the table top. The magnetic resonance image reconstructed from the acquired magnetic resonance signal has a high image quality and has a low level of artefacts due to spatial inhomogeneities of the static magnetic field because the region-of-interest is accurately placed in region of very good spatial homogeneity of the static magnetic field. The motion transverse to the support surface is generally vertically. Hence, accurate placement of the region-of-interest within the spatial homogeneity region is enabled independent of the size of the patient's body According to this invention, when a slim patient is examined (imaged), the patient carrier can be moved vertically to position this slim patient optimally in the homogeneity region. When an obese patient is examined (imaged) the patient carrier is lowered to position this obese patient optimally in the homogeneity region. Further, the patient carrier may be moveable along its longitudinal axis, generally to move the patient to be examined into and out of the examination zone of the magnetic resonance examination system. The patient carrier may also be moveable in the support surface, transverse to the longitudinal axis, i.e. generally sideways in order to position the region-of-interest accurately in the spatial homogeneity region. Thus, optionally the patient carrier is moveable both vertically and horizontally.

The support surface is the patient carrier's face onto which the patient to be examined is placed in preparation and during the examination in the examination zone. The patient carrier with its support face (which may be an integral part of it) is moveable in the direction transverse to the support face; i.e. along the normal to the support face. That is, the patient carrier defines its own coordinate system of longitudinal and lateral directions that are in the support surface and the transverse direction normal to the support surface. According to the present invention, the patient carrier is mounted such that it can be moved (in direction relative to its own frame of reference) in the transverse direction. In practice, the longitudinal direction is along the long axis of the (elongate) patient carrier, the lateral direction is sideways and the transverse direction is along the vertical axis.

In a preferred embodiment of the magnetic resonance examination system of the invention the magnet has a supporting frame and is provided with a bridge member mounted moveably in the direction transverse to the support surface to the supporting frame and wherein the bridge member supports the patient carrier. The bridge member can be easily mounted moveably to the supporting frame of the magnet. Alternatively, the bridge can also be mounted to the floor of the room or to the gradient coil or the RF body coil. The bridge member supports the patient carrier. Hence, there is no need to adapt the patient carrier to achieve motion transverse to the support surface.

In another embodiment, the magnet is a cylindrical shaped magnet with a bore in which the examination zone is located, wherein skirt pieces are provided between the bridge member or the patient carrier and bore's inner wall. The skirt pieces cover a gap between the patient carrier of the bridge member and the inner wall of the bore. In this way, it is avoided that objects could fall through that space. The skirt pieces also prevent that when during movement the gap closes attending staff's hand or fingers may be caught, notably this embodiment is safe in that finger pinching between the patient carrier and the wall of the bore is avoided. Preferably the skirt pieces are mounted in a flexible way of are made of flexible material or are formed from several flexibly coupled skirt elements. In another example the skirt pieces can be formed as inflatable skirt-members. These inflatable skirt-members can be inflated to a degree to cover the gap. This achieves that the skirt pieces continue to cover the gap, while the gap size changes during notably motion of the patient carrier transverse to its support surface. The skirt pieces, may be formed as flexibly mounted covers that are arranged over the gap between the bridge member and the inner wall of the bore. These skirt pieces may be covers of a flexible deformable material of may be flexible mounted to be moveable. The deformation or moveably allows to cover the gap while the patient carrier (carrying the patient to be examined) is moved into or out of the examination zone and ensures smooth movement of the patient carrier relative to the inner wall of the magnet bore.

In a further embodiment a drive system is provided to control the movement of the patient carrier, the drive system having one or more actuators to drive motion of the patient carrier and a drive-control module to control the actuators. This achieves the patient support to be driven into its proper position, so that there is no need for manual adjustment of the height of the patient support while carrying the patient to be examined. The drive-control module is preferably configured to drive the patient carrier to compensate motion caused by the acquisition of the magnetic resonance signals. This improves patient comfort because the patient to be examined does not or at least to a lesser extent experience any vibrations caused during the acquisition of the magnetic resonance signals. This is notably achieved when the drive control module is coupled to the gradient controller so as to control the movement of the patient carrier to compensate motion due to switching of the gradient magnetic field. Thus, vibrations that are generated by the gradient switching are compensated by the motion of the patient carrier and not transmitted onto the body of the patient to be examined.

Alternatively, the drive control module may function to intentionally independently apply vibrations to the patient support onto the body of the patient to be examined. This enables to perform MR elastography without the need for a separate oscillator the launch material waves into the body of the patient to be examined.

These and other aspects of the invention will be elucidated with reference to the embodiments described hereinafter and with reference to the accompanying drawings.

DETAILED DESCRIPTION OF THE EMBODIMENTS

Figure 1:
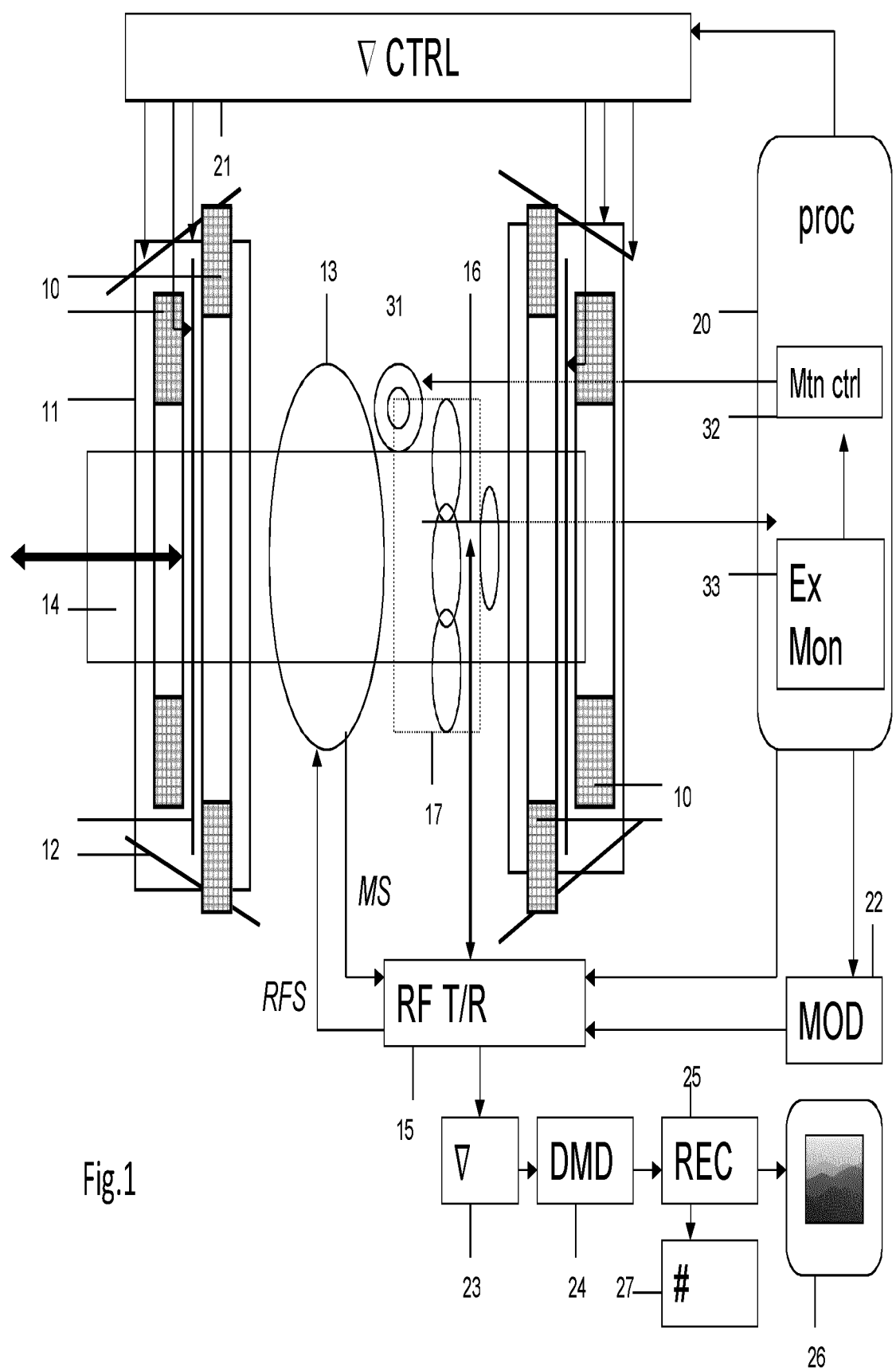
FIG. 1 shows diagrammatically a magnetic resonance imaging system in which the invention is used.

FIG. 1 shows diagrammatically a magnetic resonance imaging system in which the invention is used. The magnetic resonance imaging system includes a main magnet with a set of main coils 10 whereby the steady, uniform magnetic field is generated. The main coils are constructed, for example in such a manner that they from a bore to enclose a tunnel-shaped examination space. The patient to be examined is placed on a patient carrier which is slid into this tunnel-shaped examination space. The magnetic resonance imaging system also includes a number of gradient coils 11, 12 whereby magnetic fields exhibiting spatial variations, notably in the form of temporary gradients in individual directions, are generated so as to be superposed on the uniform magnetic field. The gradient coils 11, 12 are connected to a gradient control 21 which includes one or more gradient amplifier and a controllable power supply unit. The gradient coils 11, 12 are energised by application of an electric current by means of the power supply unit 21; to this end the power supply unit is fitted with electronic gradient amplification circuit that applies the electric current to the gradient coils so as to generate gradient pulses (also termed 'gradient waveforms') of appropriate temporal shape. The strength, direction and duration of the gradients are controlled by control of the power supply unit. The magnetic resonance imaging system also includes transmission and receiving antennae (coils or coil arrays) 13, 16 for generating the RF excitation pulses and for picking up the magnetic resonance signals, respectively. The transmission coil 13 is preferably constructed as a body coil 13 whereby (a part of) the object to be examined can be enclosed. The body coil is usually arranged in the magnetic resonance imaging system in such a manner that the patient 30 to be examined is enclosed by the body coil 13 when he or she is arranged in the magnetic resonance imaging system. The body coil 13 acts as a transmission antenna for the transmission of the RF excitation pulses and RF refocusing pulses. Preferably, the body coil 13 involves a spatially uniform intensity distribution of the transmitted RF pulses (RFS). The same coil or antenna is generally used alternately as the transmission coil and the receiving coil. Typically, a receiving coil includes a multiplicity of elements, each typically forming a single loop. Various geometries of the shape of the loop and the arrangement of various elements are possible The transmission and receiving coil 13 is connected to an electronic transmission and receiving circuit 15.

It is to be noted that is that there is one (or a few) RF antenna elements that can act as transmit and receive; additionally, typically, the user may choose to employ an application-specific receive antenna that typically is formed as an array of receive-elements. For example, surface coil arrays 16 can be used as receiving and/or transmission coils. Such surface coil arrays have a high sensitivity in a comparatively small volume. The receiving coil is connected to a preamplifier 23. The preamplifier 23 amplifies the RF resonance signal (MS) received by the receiving coil 16 and the amplified RF resonance signal is applied to a demodulator 24. The receiving antennae, such as the surface coil arrays, are connected to a demodulator 24 and the received pre-amplified magnetic resonance signals (MS) are demodulated by means of the demodulator 24. The pre-amplifier 23 and demodulator 24 may be digitally implemented and integrated in the surface coil array The demodulated magnetic resonance signals (DMS) are applied to a reconstruction unit. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses. In particular the surface receive coil arrays 16 are coupled to the transmission and receive circuit by way of a wireless link. Magnetic resonance signal data received by the surface coil arrays 16 are transmitted to the transmission and receiving circuit 15 and control signals (e.g. to tune and detune the surface coils) are sent to the surface coils over the wireless link.

The reconstruction unit derives one or more image signals from the demodulated magnetic resonance signals (DMS), which image signals represent the image information of the imaged part of the object to be examined. The reconstruction unit 25 in practice is constructed preferably as a digital image processing unit 25 which is programmed so as to derive from the demodulated magnetic resonance signals the image signals which represent the image information of the part of the object to be imaged. The signal on the output of the reconstruction is applied to a monitor 26, so that the reconstructed magnetic resonance image can be displayed on the monitor. It is alternatively possible to store the signal from the reconstruction unit 25 in a buffer unit 27 while awaiting further processing or display.

The magnetic resonance imaging system according to the invention is also provided with a control unit 20, for example in the form of a computer which includes a (micro) processor. The control unit 20 controls the execution of the RF excitations and the application of the temporary gradient fields. To this end, the computer program according to the invention is loaded, for example, into the control unit 20 and the reconstruction unit 25.

Figures 2, 3:
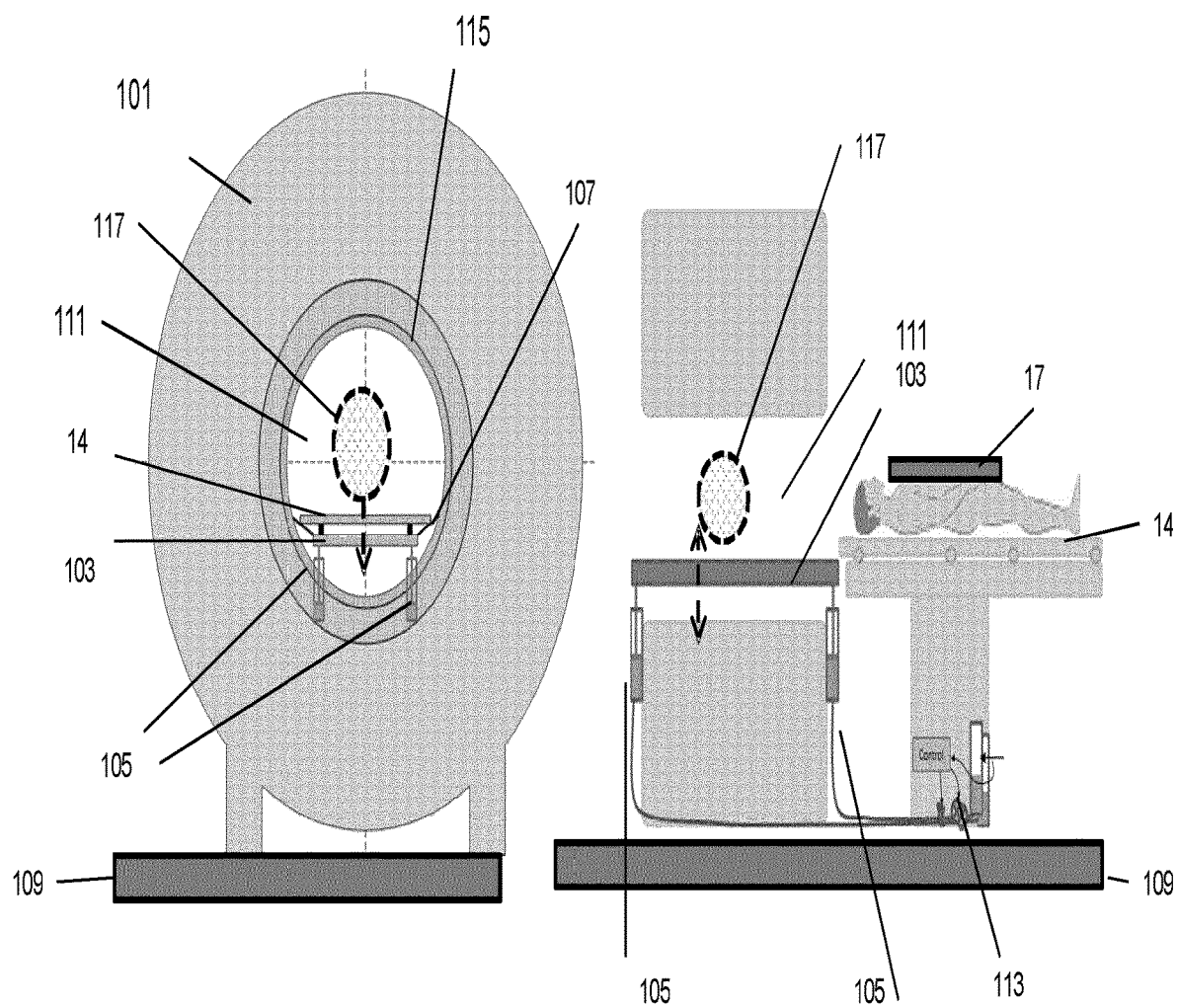
FIG. 2 shows a front elevation of a magnetic resonance imaging system in which the invention is used and FIG. 3 shows a side elevation a magnetic resonance imaging system in which the invention is used.

FIG. 2 shows a front elevation of a magnetic resonance imaging system in which the invention is used. FIG. 2 shows the magnet frame 101 in which the main coils, gradient coil and the RF body coil are mounted. The main coils are cylindrical and form the bore 115. Within the bore 115 the examination zone 111 is located from which magnetic resonance signal from the patient to be examined can be acquired. The homogeneity region 117 is a generally spherical or ellipsoidal region in which the main magnetic field has a high degree of spatial homogeneity. Typically a main magnet field homogeneity of 2 ppm over a 25 cm radius spherical volume is achieved. Also the gradient magnetic fields only have very small deviations from linearity. The magnet frame 101 is placed on the floor 109 of the examination room. The patient table top 14 is mounted on the bridge member 103. The bridge member is mounted to be moveable in the direction transverse to the surface of the table top, in this example in the vertical direction. The actuators 105 are provided mounted to the frame and operate to move the bridge member in the transverse direction, i.e. up and down as shown by the double arrows.

FIG. 3 shows a side elevation of a magnetic resonance imaging system in which the invention is used. In FIG. 3, the patient to be examined is shown on the table top 14, but still located outside the examination zone 111 of the magnetic resonance examination system. The table top 14 rests on a pedestal 113 and can be translated into the examination zone in the magnet frame 101. The RF coil array 17 is already placed on the patient's body. The RF coil array 17 may be actually be directly placed on the patient's body, or a separate coil support may be mounted to the table top 14 to which the RF coil array can be attached. The skirt pieces 107 are shown flexibly mounted to the bridge member 103 and reach onto the inner wall of the examination zone. During movement of the bridge member, the skirt pieces cover the gap between the bridge member and the inner wall and also between the table top and the inner wall. The actuators 105 are hydraulic actuators that are driven by a hydraulic system 113 that is located in the pedestal 113. Alternatively, piezoelectric actuators can be employed together with an electrical drive and control module to control the actuators to drive the bridge member to be displaced in the vertical direction. The drive and control module 113 may also be combined with the motion control 32 for controlling the table to be moved longitudinally into and out of the bore.

The invention claimed is:

1. A magnetic resonance examination system comprising:
an annular magnet which defines an annular bore therein, the annular magnet being configured to apply a static magnetic field in an examination zone in the bore, the magnet having a magnet supporting frame;
gradient coils configured to generate gradient magnetic fields in the examination zone;
a bridge mounted in the bore to the magnet supporting frame;
one or more actuators mounted between the magnet supporting frame and the bridge and operatively connected to the bridge to move the bridge in a vertical direction;
a patient carrier with a patient support surface configured to be moved into the bore and be supported by the bridge when the patient support is moved into the bore such that the patient carrier, when in the bore, moves in the vertical direction with the bridge;
a scan control processor configured to control acquisition of magnetic resonance signals when the patient carrier is disposed in the bore and control the one or more actuators to drive the bridge and the patient carrier supported thereby in the vertical direction during the acquisition of the magnetic resonance signals to compensate motion caused by switching of the gradient magnetic field during the acquisition of the magnetic resonance signals;
wherein the one or more actuators are not operatively connected to the gradient coils.

2. The magnetic resonance examination system as claimed in claim 1, further including:
skirt pieces disposed between the bridge member and an inner wall of the bore or between the patient carrier and the inner wall of the bore and configured to close a gap between the patient carrier or the bridge member and the inner wall of the bore to prevent hands or fingers from being pinched between the bridge or the patient carrier and the inner wall of the bore.

3. The magnetic resonance examination system as claimed in claim 2, wherein the skirt pieces are flexibly mounted to the bridge member or the patient carrier.

4. The magnetic resonance examination system as claimed in claim 2, wherein the skirt pieces are inflatable skirt elements.

5. The magnetic resonance examination system as claimed in claim 1, wherein the compensated motion includes vibrations and compensating for the motion includes not transmitting vibrations to the patient.

6. A magnetic resonance examination method comprising:
generating a static magnetic field in an examination zone in a bore of an annular magnet;
generating gradient magnetic fields in the examination zone with gradient coils;
supporting a patient on a patient support surface of a patient carrier;
moving the patient carrier longitudinally into the bore and onto a bridge member mounted to a supporting frame of the annular magnet; and
during an acquisition of magnetic resonance signals, moving, with actuators operatively connected to the bridge, the bridge and the patient carrier supported thereby vertically to compensate for vertical movement of the patient carrier caused by switching the gradient magnetic field during the acquisition of the magnetic resonance signals;
wherein the actuators are not operatively connected to the gradient coils.

7. The magnetic resonance examination method as claimed in claim 6, wherein the vertical movement includes vibrations.

8. The magnetic resonance examination method as claimed in claim 7, wherein compensating for the vertical movement causes the vibrations not to be transmitted to the patient.

9. The magnetic resonance examination method as claimed in claim 6, further including preventing hands or fingers from being pinched between a wall of the bore and the patient support by disposing skirt members in a gap between the wall of the bore and the patient support.

10. The magnetic resonance examination method as claimed in claim 6, further including preventing hands or fingers from being pinched between a wall of the bore and the bridge member by disposing skirt members in a gap between the wall of the bore and the bridge member.

11. A magnetic resonance examination system including an annular magnet defining a subject receiving bore therein and configured to generate a steady, uniform magnetic field therein, gradient magnetic field coils configured to generate gradient magnetic fields including a vertical gradient magnetic field in the subject receiving bore, and a whole body RF coil disposed around the subject receiving bore and configured to generate at least magnetic resonance excitation radio frequency signals into the bore and further comprising:
a patient carrier supported by a pedestal exterior to the bore and configured to support the subject thereon and to move horizontally into and out of the bore;
local radio frequency receive coils mounted to at least one of the subject and the patient carrier in a fixed relationship to the subject,
a bridge member disposed in the bore and operatively connected to, and supported by, actuators, the bridge member being configured to support the patient carrier when the patient carrier is disposed in the bore, the actuators being configured to vertically move the bridge member along with the patient carrier, the subject supported thereon, and the local radio frequency coils vertically;

a computer controller configured to:

control the whole body RF coil, the gradient magnetic field coils and the local radio frequency receive coils to acquire the magnetic resonance signals from the subject, the generation of the gradient magnetic field during acquiring the magnetic resonance signals causing vibratory motion, control the actuators to move the bridge member to compensate for the vibratory motion such that the vibratory motion is not transmitted to the subject during acquiring the magnetic resonance signals;

wherein the actuators are not operatively connected to the gradient magnetic field coils.

12. The magnetic resonance examination system as claimed in claim 11, further including:

skirt pieces disposed between the bridge member and an inner wall of the bore or between the patient carrier and the inner wall of the bore and configured to close a gap between the patient carrier or the bridge member and the inner wall of the bore to prevent hands or fingers from being pinched between the bridge or the patient carrier and the inner wall of the bore.

13. The magnetic resonance examination system as claimed in claim 12, wherein the skirt pieces are flexibly mounted to the bridge member or the patient carrier.

14. The magnetic resonance examination system as claimed in claim 12, wherein the skirt pieces are inflatable skirt elements.

* * * * *